United States Patent [19]
Stoop et al.

[11] Patent Number: 5,999,853
[45] Date of Patent: Dec. 7, 1999

[54] DUAL CHAMBER PACEMAKER WITH SINGLE PASS LEAD AND WITH BIPOLAR AND UNIPOLAR SIGNAL PROCESSING CAPABILITY

[75] Inventors: Gustaaf A. P. Stoop, Dieren, Netherlands; Werner P. Wohlgemuth, Neukirchen, Germany; Hendrikus A. Westendorp, Zutphen, Netherlands

[73] Assignee: Vitatron Medical, B.V., Dieren, Netherlands

[21] Appl. No.: 09/032,977

[22] Filed: Mar. 2, 1998

[51] Int. Cl.$^6$ .......................... A61N 1/368; A61N 1/362
[52] U.S. Cl. ................................. 607/9; 607/123
[58] Field of Search ................. 607/9, 122, 123

[56] References Cited

U.S. PATENT DOCUMENTS

| | | |
|---|---|---|
| 4,549,548 | 10/1985 | Wittkampf et al. . |
| 5,172,694 | 12/1992 | Flammang et al. . |
| 5,193,550 | 3/1993 | Duffin . |
| 5,265,601 | 11/1993 | Mehra . |
| 5,312,445 | 5/1994 | Nappholz . |
| 5,330,512 | 7/1994 | Hauck et al. . |
| 5,450,846 | 9/1995 | Goldreyer . |
| 5,522,855 | 6/1996 | Hoegnelid ................................ 607/9 |
| 5,571,143 | 11/1996 | Hoegnelid et al. ...................... 607/9 |
| 5,674,274 | 10/1997 | Morgan et al. ....................... 607/123 |
| 5,755,738 | 5/1998 | Kim et al. ................................. 607/9 |

OTHER PUBLICATIONS

Nava et al, "Chapter 9.1:Single Lead VDD Pacing", *The Foundations of Cardiac Pacing, Pt. II: An Illustrated Practical Guide to Rate, Variable Pacing*, Futura Publishing, © 1999.

*Primary Examiner*—William E. Kamm
*Assistant Examiner*—Carl H. Layno
*Attorney, Agent, or Firm*—Thomas F. Woods; Harold Patton; Michael J. Jaro

[57] ABSTRACT

There is provided an implantable cardiac pacing system, having multiple sensing channels for sensing spontaneous cardiac signals which arise between respective different pairs of electrodes. In a preferred embodiment, the system utilizes a single pass VDD-type lead, having at least one atrial ring electrode for sensing atrial signals, and at least a distal tip electrode positioned in the right ventricle for sensing ventricular signals. Sensing channels concurrently process signals between the atrial ring and the pacemaker can (the indifferent electrode); the ventricular tip electrode and the pacemaker can; and the between the atrial ring and the ventricular tip. One or more additional electrode pairs can also be employed. Enable signals selectively enable the channels to be used for concurrent processing of the signals. The signal processing embodies both pattern recognition and timing, for analysis and interpretation of the type of event which gives rise to the different concurrent signals on the respective different channels.

19 Claims, 5 Drawing Sheets

| P: | P-WAVE |
|---|---|
| R: | R-WAVE |
| F: | FAR FEILD R-WAVE |
| AR: | ATRIAL RING TO CAN |
| VT: | VENTRICULAR TIP TO CAN |
| RT: | ATRIAL RING TO VENTRICULAR TIP |

# 5,999,853

DUAL CHAMBER PACEMAKER WITH SINGLE PASS LEAD AND WITH BIPOLAR AND UNIPOLAR SIGNAL PROCESSING CAPABILITY

FIELD OF THE INVENTION

This invention lies in the area of cardiac pacing systems and, more particularly, pacemaker systems with concurrent unipolar and bipolar sensing and comparative signal processing.

BACKGROUND OF THE INVENTION

In the field of cardiac pacemakers, there is a continuing need to provide an improved sensing system for accurately sensing and identifying patient heartbeat signals. As is well known, sensing of spontaneously occurring heartbeat signals is important for the proper operation of the pacemaker. Particularly for dual chamber pacing systems, it is important to be able to accurately identify sensed signals. For example, it is important to know when a signal that is sensed from the patient's atrium is of ventricular origin, i.e., a far field R-wave; or when a sense channel is missing a signal due to undersensing. Particularly in the case of a VDD single pass pacing system, the sensing from the atrial electrode or electrodes may be suspect, i.e., the source of the signal may be ambiguous.

It is known that unipolar sensing can provide certain sensing that bipolar sensing is unable to provide, and vice versa. What is needed is a pacemaker system providing selectable concurrent bipolar and unipolar sensing, and selectable switching for enabling the pacemaker to process the desired signal senses so as to optimize available information and provide for enhanced interpretation of the nature of sensed signals.

SUMMARY OF THE INVENTION

There is provided a dual chamber pacing system for cardiac pacing, preferably a system with a single pass lead providing at least one ring electrode positioned in the patient's atrium, and at least a distal tip electrode for positioning in the patient's right ventricle. The system senses spontaneous heartbeat signals between respective pairs of the lead electrodes and the indifferent electrode which is suitably positioned on the can or housing of the implanted pacemaker. At least three signals are selected cyclically for concurrent processing, e.g., the AR signal, atrial ring to can; the VT signal, ventricular tip to can; and RT, atrial ring to ventricular tip. In addition, a second spaced ring can be positioned in each of the atrium and ventricle, for bipolar sensing in each of those heart chambers.

The selected signals are sensed concurrently and processed, either serially or in parallel, for interpretation of the type of event represented by the sensed signal. In a preferred embodiment, each sensed signal is digitized and processed through the digital signal processor for comparing the patterns of the respective signals, as well as the respective timing of the signals. Based on the pattern and/or timing processing, the concurrent signals are interpreted to represent a P-wave, R-wave or "other," where other may be simply noise, a far field R-wave, or an ectopic beat.

DESCRIPTION OF THE PREFERRED EMBODIMENTS

In the following description of the preferred embodiments, the invention is illustrated in the embodiment of a pacing system with a single pass lead, enabling VDD pacing. While this is a currently important embodiment, it is emphasized that the invention is not limited to such a single lead system, and may embrace conventional dual chamber or multi-chamber pacing systems with separate leads dedicated to each chamber to be paced and/or sensed.

Figure 1:
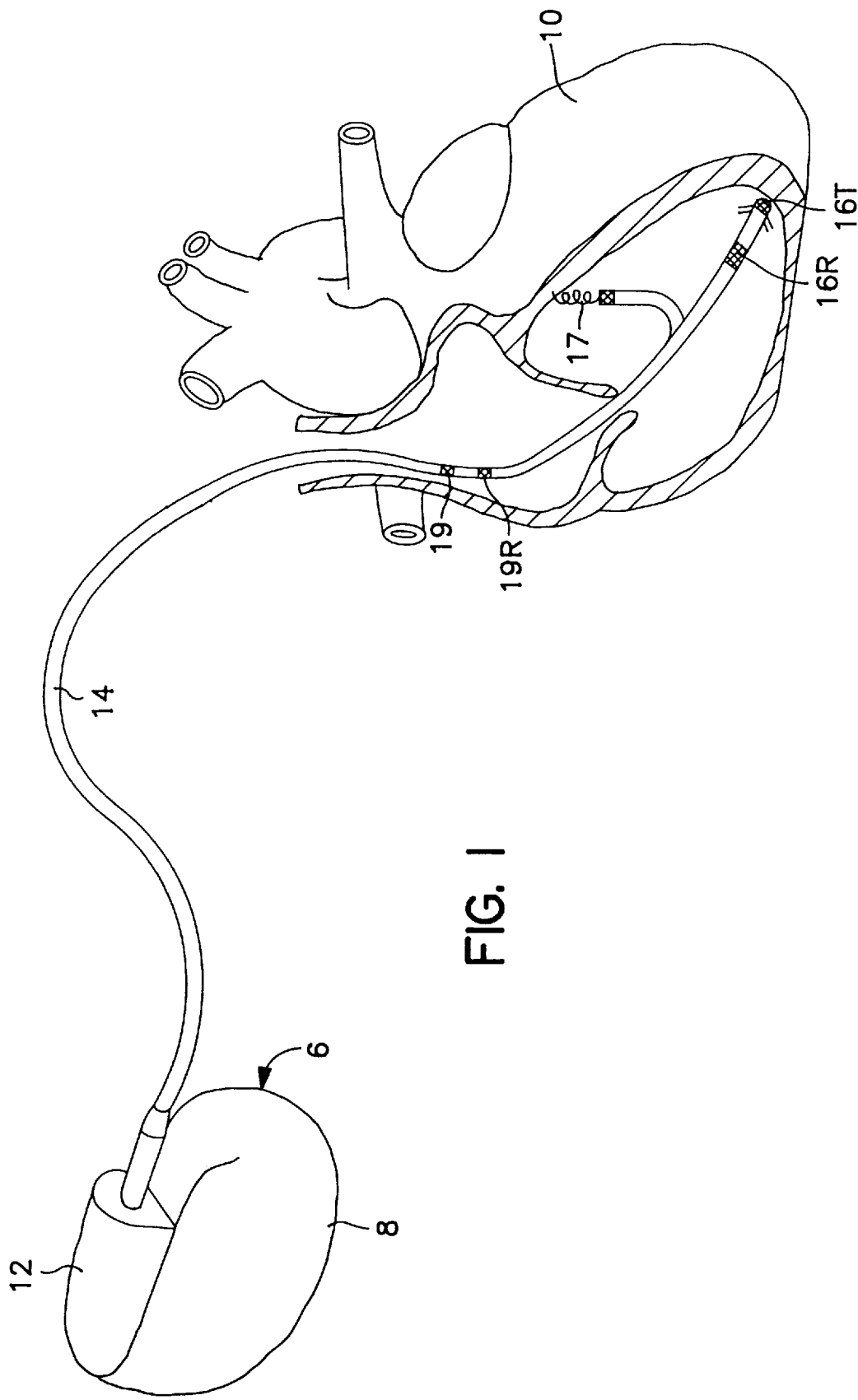
FIG. 1 is a diagrammatic representation of a pacing system in accordance with this invention, providing an implantable pacemaker and a single pass lead shown positioned within a patient's heart.

Referring specifically to FIG. 1, there is illustrated an implantable pacemaker 6, having a housing 8, a portion of which is used as an indifferent electrode for unipolar pacing and sensing, in a well known manner. Connector block 12 receives the proximal end of lead 14, illustrated as a single pass lead. As shown, the lead has a tip electrode 16T, positioned at the ventricular apex. A ring electrode 16R may be positioned on the lead just proximal to the distal electrode, to provide bipolar ventricular pacing and/or sensing. Shown in dashed lines is an alternate embodiment of the lead, whereby the lead distal electrode 17 is screwed into the right ventricular outflow track (RVOT) for RVOT pacing. As used herein, the term distal tip electrode includes a conventional tip electrode; a helical screw-type electrode; or any electrode form at or about at the distal end of the lead. Also shown on the lead 14 is a ring electrode 19, positioned sufficiently proximal to the distal electrode so that it is placed within the patient's right atrium. As illustrated, the lead has a preformed bend or is introduced with sufficient slack so as to carry the atrial ring electrode 19 into closer proximity to the right free atrial wall. In an embodiment which includes atrial bipolar pacing and/or sensing, another ring electrode, illustrated at 19R, is spaced so as to also be positioned in the atrium when the distal tip electrode is positioned at the ventricular apex.

Figure 2:
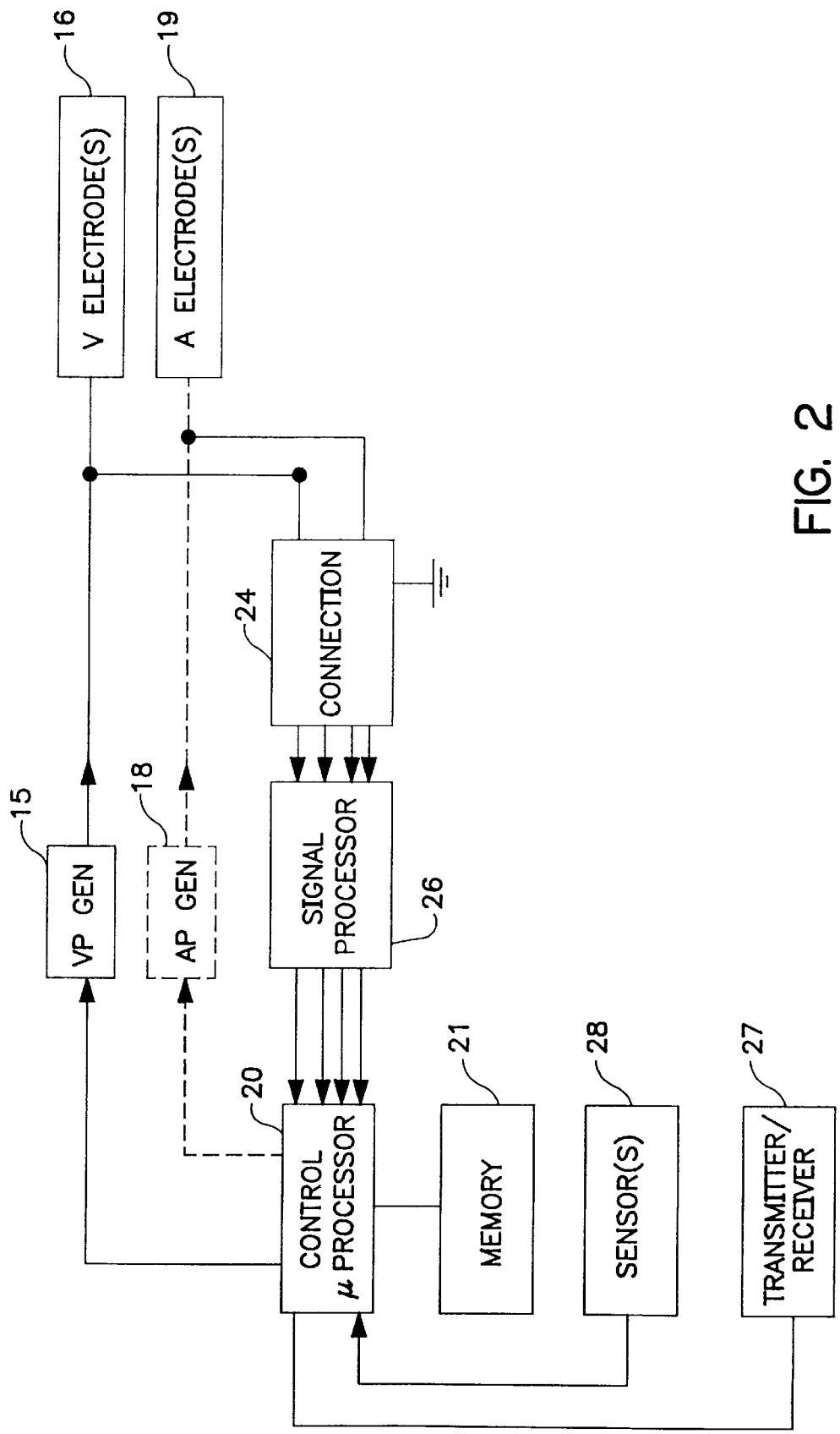
FIG. 2 is a block diagram of the primary components of a pacemaker in accordance with this invention.

Referring now to FIG. 2, there is shown a block diagram of the primary components of an implantable pacemaker in accordance with this invention. A ventricular pulse generator, shown at 15, delivers ventricular pacing pulses to one or more ventricular electrodes, illustrated at 16. For unipolar pacing, stimulus pulses from generator 15 are delivered between tip electrode 16T and the pacemaker can; for bipolar pacing the pulses are delivered between electrodes 16T and 16R. The timing and other parameters of the stimulus pulses are controlled by control block 20, which suitably includes a microprocessor, which microprocessor in turn is operatively connected with memory 21. Also shown in dashed lines is an atrial pulse generator 18, which would be included in a dual chamber DDD pacemaker, the pacing pulses from which are delivered to one or more atrial electrodes 19. A sensor or sensors 28 provide parameter signals which are connected to block 20 for providing rate responsive pacing, in a known manner. Further, a transmitter/receiver 27 is in two-way communication with block 20, for receiving program instructions from an external programmer, and also for downloading collected data from the pacemaker to the programmer.

Still referring to FIG. 2, the electrodes 16, 19 are shown connected to process block 26, which is described in greater detail in connection with FIG. 3. Note that two ventricular electrodes may provide two signals conducted to connection block 24 on respective conductors within the ventricular lead, for a bipolar embodiment. Likewise, signals sensed by atrial electrode 19, or electrodes 19, 19R, are connected through to block 26. Ground is represented as also being connected to block 24, and in this case ground is suitably the pacemaker can, which acts as an indifferent electrode for unipolar sensing and/or pacing. The signals coming into block 24 are connected to control block 20, for processing and interpretation.

Figure 3:
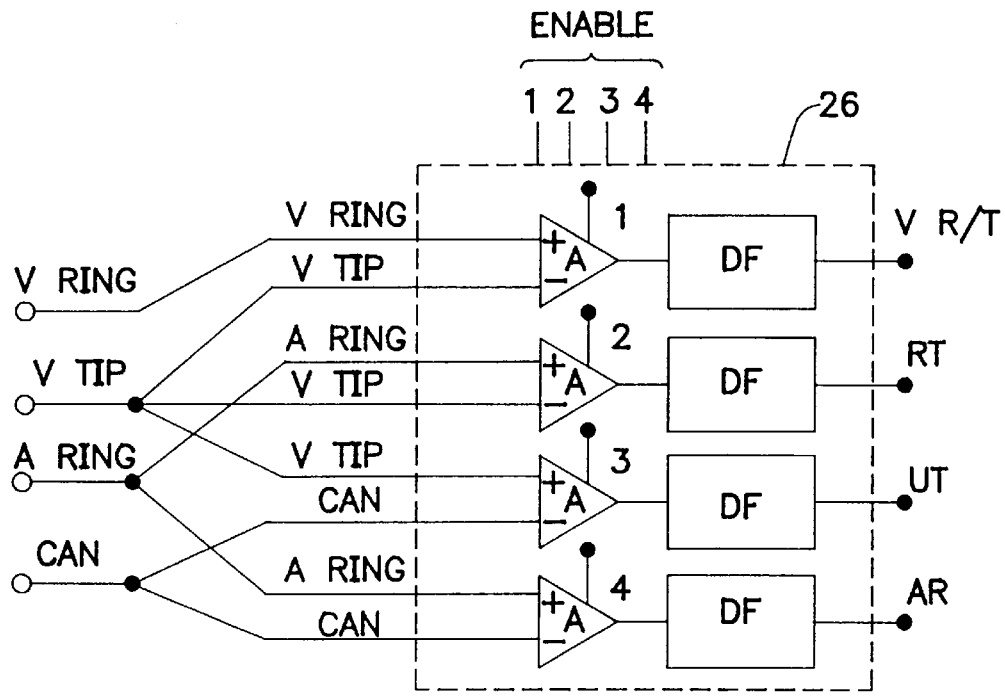
FIG. 3 is a circuit diagram showing a multiple channel signal sensing circuit for concurrent sensing of multiple signals, in accordance with this invention.

Referring now to FIG. 3, there are shown four electrode inputs which are connected in pairs to the four processing channels that are illustrated. These inputs are V RING, which is electrode 16R in FIG. 1; V TIP, electrode 16T; A RING, electrode 19 or 19R; and CAN, which is part of housing 8 of the pacemaker. As illustrated, the processing channels in processor 26 are V RING—V TIP (V R/T); A RING—V TIP (R/T); V TIP—CAN (VT); and A RING—CAN (AR). For each available channel, processor 26 includes an amplifier(A) and a digital filter (DF) which filters and digitizes the signal for subsequent digital processing in control microprocessor block 20. Thus, according to the enabling signals inputted on the Enable lines designated 1–4, any one or more of the output signals V R/T, RT, VT, and AR can be provided. The Enable signals are provided from control block 20. Also, although not illustrated, a second atrial ring may be used, providing for a bipolar AR—AR signal from electrodes 19, 19R. In the preferred embodiment of the system of this invention, the last three of these signals are enabled and processed; the enable signals are programmable through transmitter/receiver 27.

Figure 4A:
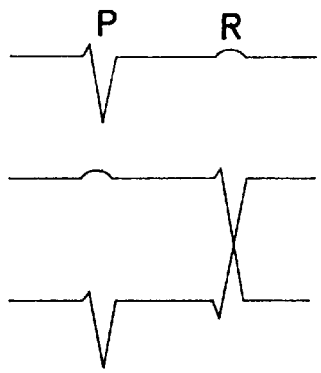
FIG. 4a is a series of timing diagrams showing sensing AR, VT and RT signals.
Figure 4B:
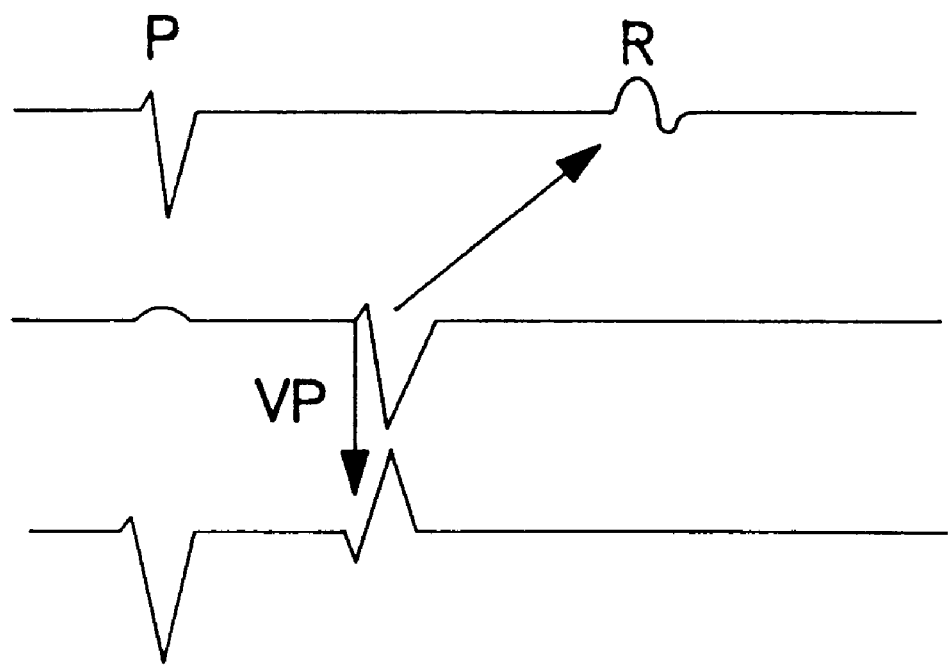
FIG. 4b illustrates atrial sensing of a far field R-wave (FFRW), following delivery of a ventricular pace pulse (VT).

Referring to FIG. 4a, there is shown a series of timing diagrams illustrating in stylized form the sensed AR, VT and RT signals. The AR signal, between a floating atrial ring and can, provides a relatively large P-wave, and relatively small R-wave. The VT signal, between the ventricular tip electrode and the can, shows a very small P-wave, and a relatively large negative going R-wave. The RT signal, between the atrial ring and the ventricular tip, shows both a large negative going P-wave and a large positive going R-wave. In FIG. 4b, there are shown signals sensed in the AR, VT and RT channels when a ventricular pace pulse is delivered, showing the far field R wave as sensed in the AR channel.

Still referring to FIG. 4a, it can be seen that comparing the time of occurrence of signals on the AR, VT and RT channels leads to the following decisions which are carried out in control block 20:

TABLE I

| RT | AR | VT | Decision |
|---|---|---|---|
| — | — | 1 | Undefined (noise or muscle potentials) |
| — | 1 | — | Undefined (noise or muscle potentials, FFRW) |
| — | 1 | 1 | Undefined (noise or muscle potentials) |
| 1 | — | — | Undefined (noise or muscle potentials) |
| 1 | — | 1 | R-sense |
| 1 | 1 | — | P-sense (or FFRW) |
| 1 | 1 | 1 | R-sense |

As seen from Table I, there are three situations where a decision can be made on the basis of timing alone, i.e., the source of the signal can be reliably determined. When an RT and VT signal are both present, but there is no AR, the underlying event is a QRS, or R-sense. When an RT and AR are present, but no VT, the underlying event is a P-sense (or FFRW). And, when RT, AR and VT are all present, the underlying event must be an R-sense. When only an AR is present, the decision is undefined. Since the signal has appeared on the AR channel, it could be an FFRW; otherwise it is noise or muscle potentials. Likewise, when only a VT signal is present; only an RT signal is present; or AR and VT are present without RT, the signal is undefined. In these situations, an analysis based upon the signal pattern, or morphology, may result in a definitive determination, i.e., an interpretation of the underlying event which can be relied upon.

Figure 5A:
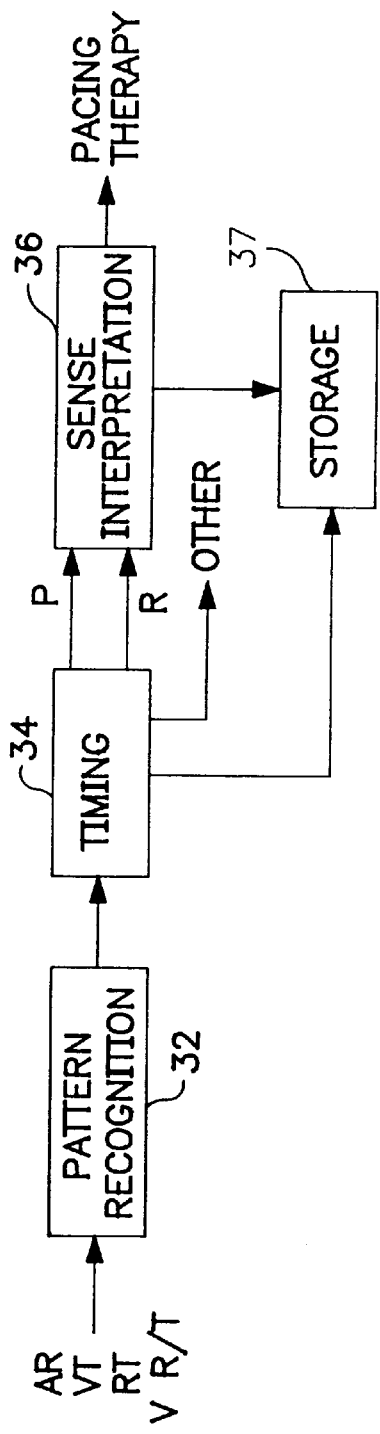
FIG. 5a is a block diagram showing the primary functions in concurrent serial processing of three or more sensed signals, in accordance with this invention.

Referring now to FIG. 5a, there is shown a block diagram of steps taken by control block 20, in conjunction with memory, for serially processing of signals received concurrently by three or four channels, as indicated. At 32, the signals appearing on the various lines, or channels are digitally analyzed or compared for pattern recognition. Thus, in this step each signal can be compared to one or more stored patterns representative of different types of cardiac signals; and/or the patterns can be compared to each other. The resulting pattern data is stored, and then the signals are compared at 34 in terms of timing sequence, as discussed in connection with Table I above. At this point, based on the pattern recognition and timing processing steps, the signal is identified as a P-wave, an R-wave or an "other" type of wave. At the same time, the result is stored in storage 37. For an event determined to be a P-wave or an R-wave, a sense interpretation is made at 36, i.e., the P-wave or the R-wave is classified so as to enable the pacemaker logic to proceed with appropriate pacing therapy.

Figure 5B:
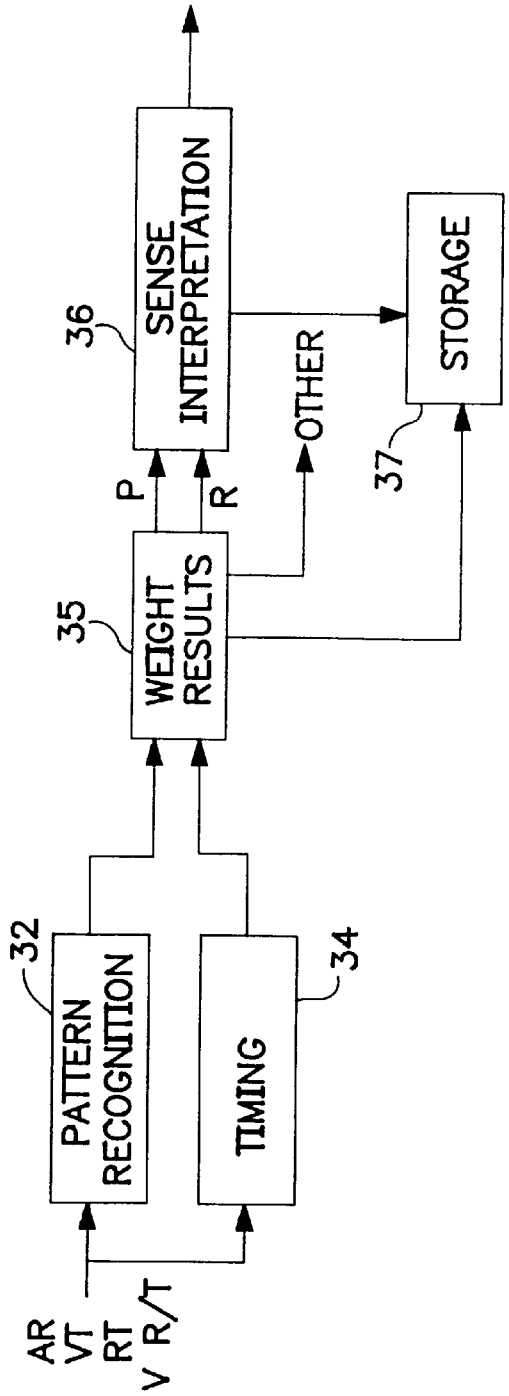
FIG. 5b is a block diagram showing the concurrent parallel processing of three or more sensed signals, in accordance with this invention.

Referring to FIG. 5b, there is shown a block diagram of signal processing undertaken within the microprocessor for parallel processing of the concurrent channel information. As indicated here, the pattern recognition processing as shown at 32 and the timing processing as shown at 34 are done in parallel. The results of the pattern recognition and timing processing are weighted at 35, in accordance with predetermined weighting factors. Following this, sense interpretation is again made at 36, and data is stored at storage block 37.

We claim:

1. A dual chamber pacing system for cardiac pacing of a patient, comprising:
   pulse means for generating pacing pulses;
   a single pass lead for delivering pacing pulses to the patient's heart and for sensing cardiac signals from the patient's atrium and ventricle, said lead comprising at least one electrode positioned thereon for placement in said atrium and one electrode positioned thereon for placement in said ventricle;

an indifferent electrode;

sensing means for sensing signals between respective pairs of said atrial, ventricular and indifferent electrodes;

enabling means for cyclically enabling one or more of said signals for processing, said enabling means comprises programmable means for cyclically enabling at least two signals sensed at two respective pairs of said electrode; and processing means for processing said enabled signals for interpreting the type of event represented by said each said sensed signal.

2. The system as described in claim 1, wherein said enabling means comprises means for enabling three respective sensed signals for processing.

3. The system as described in claim 2, comprising data means for accumulating data relating to interpretation of sensed signals.

4. The system as described in claim 1, wherein said system comprises an implantable pacemaker, said pacemaker having a housing, and said indifferent electrode being a portion of said housing.

5. The system as described in claim 1, wherein said processing means comprises digitizing means for digitizing said sensed signals, and pattern means for analyzing the patterns of said signals.

6. The system as described in claim 1, wherein said processing means comprises timing means for comparing the relative timing of said at least two signals and for cyclically interpreting the event represented by said at least two signals.

7. The system as described in claim 1, wherein said single pass lead comprises a distal tip electrode and a ventricular ring electrode placed thereon for positioning in the ventricle, and wherein said sensing means comprises ventricular bipolar means for sensing signals from said tip and ventricular ring electrodes.

8. The system as described in claim 1, wherein said processing means comprises pattern recognition means for processing said signals to determine their patterns, timing means for processing said signals to compare their relative timing, weighing means for weighing the significance of said pattern recognition and said relative timing to provide weighed data, and interpretation means for interpreting the event represented by said processed signals in accord with said weighed data.

9. The system as described in claim 8, comprising storage means for storing data representative of said weighed data and interpreted events, and wherein a selection means comprises adjust means for adjusting said selection as a function of said stored data, said storage means and said selection means coupled with said processing means.

10. A cardiac pacing system for pacing a patient's heart, comprising:

pulse generator means for generating pacing pulses;

lead means for delivering pacing pulses to at least one chamber of the patient's heart, and for obtaining cardiac signals from the patient's atrium and ventricle, said lead means having an atrial electrode for obtaining signals from said patient's atrium and a ventricular electrode for obtaining signals from the patient's ventricle;

an indifferent electrode;

sense means for concurrently sensing any cardiac signals obtained from any one of the three respective pairs of said electrodes;

and comparing means for comparing said sensed signals to interpret the underlying cardiac activity which caused said any sensed signals, wherein said comparing means comprises timing means for comparing the relative timing of selected ones of said signals and pattern means for analyzing the patterns of selected ones of said signals, and further comprising programming means for programming which signals are operated on by said timing means and said pattern means.

11. The pacing system as described in claim 10, wherein said pulse generator, sense means and comparing means are housed in a can, and a portion of said can provides said indifferent electrode, said lead means has an atrial ring electrode and a ventricular tip electrode, and said sensing means has AR means for sensing AR signals between said atrial ring electrode and said can; RT means for sensing RT signals between said atrial ring electrode and said ventricular tip electrode; and VT means for sensing VT signals between said ventricular tip electrode and said can.

12. The pacing system as described in claim 11, wherein said lead means comprises a single pass lead on which said atrial ring electrode and said ventricular tip electrode are placed.

13. The pacing system as described in claim 12, wherein said single pass lead has a ventricular ring electrode placed thereon just proximal to said tip electrode, and said sensing means comprises V R/T means for sensing bipolar R/T signals from the patient's ventricle.

14. The pacing system as described in claim 10, wherein said lead means comprises a third electrode for positioning in the patient's heart, and said sensing means comprises means for concurrently sensing any cardiac signals from any respective pair of electrodes selected from said three electrodes and said indifferent electrode.

15. The pacing system as described in claim 14, comprising selection means for selecting which pairs of said electrodes are sensed.

16. The pacing system as described in claim 10, wherein said comparing means comprises timing means for comparing the timing of concurrently sensed signals from respective pairs of said electrodes.

17. The pacing system as described in claim 10, wherein said comparing means comprises morphology means for comparing the morphology of said respective signals.

18. The pacing system as described in claim 17, wherein said sensing means comprised digitizing means for digitizing said sensed signals, and wherein said morphology means comprises digital processing means for processing said signals.

19. The pacing system as described in claim 10, wherein said lead means comprises a ventricular lead having a tip electrode at its distal end, and an atrial lead having at least one electrode positioned for sensing atrial signals.

* * * * *